(12) United States Patent
Stasch et al.

(10) Patent No.: US 6,919,345 B2
(45) Date of Patent: Jul. 19, 2005

(54) SULFONATE SUBSTITUTED PYRAZOL PYRIDINE DERIVATIVES

(75) Inventors: Johannes-Peter Stasch, Solingen (DE); Achim Feurer, Wilhelmsfeld (DE); Stefan Weigand, Wuppertal (DE); Elke Stahl, Bergisch Gladbach (DE); Dietmar Flubacher, Freiburg (DE); Cristina Alonso-Alija, Haan (DE); Frank Wunder, Wuppertal (DE); Dieter Lang, Velbert (DE); Klaus Dembowsky, Munich (DE); Alexander Straub, Wuppertal (DE); Elisabeth Perzborn, Wuppertal (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/477,446
(22) PCT Filed: Apr. 30, 2002
(86) PCT No.: PCT/EP02/04733
§ 371 (c)(1), (2), (4) Date: Apr. 22, 2004
(87) PCT Pub. No.: WO02/092596
PCT Pub. Date: Nov. 21, 2002

(65) Prior Publication Data
US 2004/0171832 A1 Sep. 2, 2004

(30) Foreign Application Priority Data
May 11, 2001 (DE) .......... 101 22 894

(51) Int. Cl.[7] ............ C07D 471/04; A71K 31/4162
(52) U.S. Cl. ............ 514/256; 514/269; 544/298; 544/327; 544/328
(58) Field of Search ............ 544/298, 327, 544/328; 514/269, 256

(56) References Cited

U.S. PATENT DOCUMENTS

| | | | |
|---|---|---|---|
| 6,180,656 B1 | 1/2001 | Furstner et al. | 514/406 |
| 6,451,805 B1 | 9/2002 | Straub et al. | 514/269 |
| 6,462,068 B1 | 10/2002 | Straub et al. | 514/403 |
| 6,743,798 B1 | 6/2004 | Straub et al. | 514/210 |

FOREIGN PATENT DOCUMENTS

| | | | |
|---|---|---|---|
| DE | 19834045 | 2/2000 | |
| DE | 19834047 | 2/2000 | |
| DE | 10057751 | 5/2002 | |
| WO | 9816223 | 4/1998 | ......... A61K/31/415 |
| WO | 9816507 | 4/1998 | |
| WO | 9823619 | 6/1998 | ......... C07D/487/04 |
| WO | 0006567 | 2/2000 | ......... C07D/471/04 |
| WO | 0006568 | 2/2000 | ......... C07D/471/04 |
| WO | 0006569 | 2/2000 | ......... C07D/471/04 |
| WO | 0021954 | 4/2000 | ......... C07D/401/14 |

OTHER PUBLICATIONS

Prandoni, The treatment of venous thromboembolic disorders: new challenges and opportunities, Journal of Hematology, vol. 88(05):610–613, May 2003.*
Wolin et al., Oxidant–Nitric Oxide Signalling Mechanisms in Vascular Tissue, Biochemistry (Moscow), vol. 63, No. 7, 810/958, 1998.*
Layzer, Degenerative Diseases of the Nervous System, Cecil Textbook of Medicine, 20th Edition, vol. 2, pp. 2050–2057, 1996.*
Damasio, Alzheimer's Disease and Related Dementias, Cecil Textbook of Medicine, 20th Edition, vol. 2, pp. 1992–1996, 1996.*
Fisker, PubMed Abstract (J. Endocrinol. Invest. 22(5 Suppl):89–93, 1999.*
Ko et al., YC–1, a Novel Activator of Platelet Guanylate Cyclase, Blood, 84, 4226–4233 (1994).
Mulsch, et al., Effect of YC–1, an NO–independent, Superoxide–Sensitive Stimulator of Soluble Guanylyl Cyclase, on Smooth Muscle Responsiveness to Nitrovasodilators, Brit. J. Pharm. 120, 681–689 (1997).
Glass et al., Stimulation of Human Platelet Guanylate Cyclase by Fatty Acids, J. Biol. Chem., 252, 1279–1285 (1977).
Pettibone et al., A Structurally Novel Stimulator of Guanylate Cyclase with Long–lasting Hypotensive Activity in the Dog, European J. Pharm. 116, 307–312 (1985).
Yu et al., Vasorelaxant Effect of Isoliquiritigenin, a Novel Soluble Guanylate Cyclase Activator, in Rat Aorta, Brit. J. Pharm. 114, 1587–1594 (1995).

* cited by examiner

Primary Examiner—Deepak Rao

(57) ABSTRACT

This invention relates to pyrazol pyridine derivatives of formula (I)

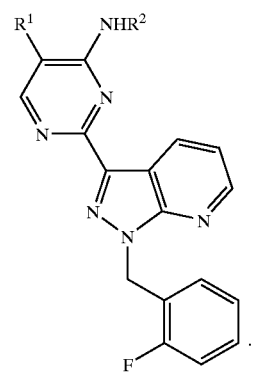

wherein $R^1$ is a radical of the formula $-O-SO_2-R^3$ in which $R^3$ is optionally substituted $C_{1-6}$—alkyl, optionally substituted $C_{3-8}$—cycloalkyl, or optionally substituted phenyl; $R^2$ is H, optionally substituted $C_{1-6}$—alkyl $-CO-$ or optionally substituted $C_{1-6}$—alkyl—$SO_2-$; as well as salts, stereoisomers, tautomers, and hydrates thereof. Pharmaceutical compositions containing these materials and methods of using them in medical treatment are also described and claimed.

10 Claims, No Drawings

SULFONATE SUBSTITUTED PYRAZOL PYRIDINE DERIVATIVES

This application is a 371 of PCT/EP02/04733 filed Apr. 30, 2002.

The present invention relates to novel chemical compounds which stimulate soluble guanylate cyclase, to the preparation thereof and to the use thereof as medicaments, in particular as medicaments for the treatment of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triposphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke, and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569 and WO 00/21954 describe pyrazolopyridine derivatives as stimulators of soluble guanylate cyclase. Also described in these patent applications are pyrazolopyridines having a pyrimidine residue in position 3. Compounds of this type have very high in vitro activity in relation to stimulating soluble guanylate cyclase. However, it has emerged that these compounds have some disadvantages in respect of their in vivo properties such as, for example, their behavior in the liver, their pharmacokinetic behavior, their dose-response relation or their metabolic pathway.

It was therefore the object of the present invention to provide further pyrazolopyridine derivatives which act as stimulators of soluble guanylate cyclase but do not have the disadvantages, detailed above, of the compounds from the prior art.

This object is achieved according to the present inventions by the compounds as claimed in claim 1. These novel pyrazolopyridine derivatives are distinguished by a pyrimidine residue in position 3, which has a particular substitution pattern, namely a sulfonate residue in position 5 of the pyrimidine ring and an amino group in position 4 of the pyrimidine ring.

The present invention specifically relates to compounds of the formula (I)

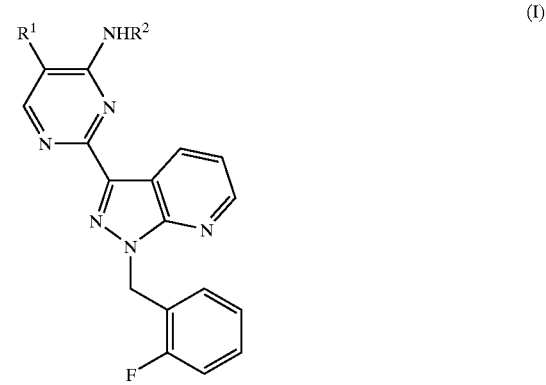

(I)

in which
R$^1$ is a radical of the formula —O—SO$_2$—R$^3$,
  where
  R$^3$ is a radical from the group consisting of optionally substituted C$_{1-6}$-alkyl, optionally substituted C$_{3-8}$-cycloalkyl, or optionally substituted phenyl;
R$^2$ is H, optionally substituted C$_{1-6}$-alkyl-CO or optionally substituted C$_{1-6}$-alkyl-SO$_2$—;
and salts, isomers and hydrates thereof.

Preference is given according to the present invention to compounds of the formula (I) in which
R$^1$ is a radical of the formula —O—SO$_2$—R$^3$,
  where
  R$^3$ is a radical from the group consisting of C$_{1-6}$-alkyl which is optionally substituted by one to three halogen radicals, or C$_{3-8}$-cycloalkyl;
R$^2$ is H, C$_{1-6}$-alkyl-CO which is optionally substituted by one to three halogen radicals, or C$_{1-6}$-alkyl-SO$_2$— which is optionally substituted by one to three halogen radicals;
and salts, isomers and hydrates thereof.

Particular preference is given in this connection to compounds of the formula (I) in which
R$^1$ is a radical of the formula —O—SO$_2$—R$^3$,
  where R³ is a radical from the group consisting of methyl, ethyl, n-propyl, isopropyl, n-butyl, n-pentyl, 1,1,1-trifluoro-4-n-butyl, chloromethyl or cyclopropyl;
R² is H or CH₃CO;
and salts, isomers and hydrates thereof.

The compounds of the invention of the general formula (I) may also exist in the form of their salts. Salts which may generally be mentioned here are those with organic or inorganic bases or acids.

For the purposes of the present invention, physiologically acceptable salts are preferred. Physiologically acceptable salts of the compounds of the invention may be salts of the substances of the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds of the invention which have a free carboxyl group. Particularly preferred examples are sodium, potassium, magnesium or calcium salts, and ammonium salts derived from ammonia or organic amines such as, for example, ethylamine, di- or triethylamine, di- or triethanolamine, dicyclohexylamine, dimethylaminoethanol, arginine, lysine or ethylenediamine.

The compounds of the invention may exist in stereoisomeric forms which either are related as image and mirror image (enantiomers) or which are not related as image and mirror image (diastereomers). The invention relates both to the enantiomers or diastereomers and to the mixtures thereof in each case. The racemic forms can, just like the diastereomers, be separated in a known manner, for example by chromatographic separation, into the stereoisomerically pure constituents. Double bonds present in the compounds of the invention may be in the cis or trans configuration (Z or E form).

Certain compounds may moreover exist in tautomeric forms. This is known to the skilled worker, and the scope of the invention likewise covers such compounds.

The compounds of the invention may additionally occur in the form of their hydrates, where the number of water molecules bound to the molecule depends on the particular compound of the invention.

Unless otherwise indicated, for the purposes of the present invention the substituents generally have the following meaning:

Alkyl is generally a straight-chain or branched hydrocarbon radical having 1 to 6 carbon atoms. Examples which may be mentioned are methyl, ethyl, propyl, isopropyl, butyl, isobutyl, pentyl, isopentyl, hexyl, isohexyl.

Cycloalkyl is generally a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

Halogen is for the purposes of the invention fluorine, chlorine, bromine and iodine.

The compounds of the invention of the formula (I) can be prepared by reacting the compound of the formula (II)

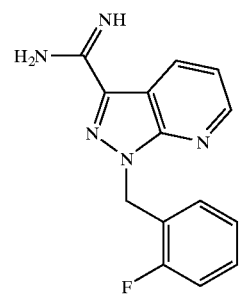

with compounds of the formula (III)

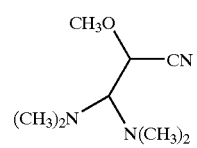

in an organic solvent in the presence of a base with heating and subsequent conversion of the ether group into the free hydroxyl group to compounds of the formula (IV)

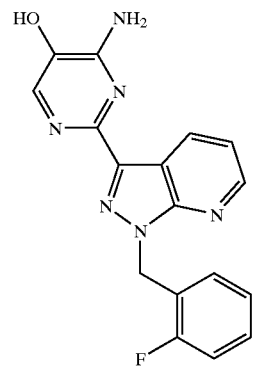

and subsequent reaction with compounds of the formula X—SO₂—R² in which

X is a leaving group which can be replaced by a hydroxyl group;

R² has the meaning indicated above;

in an organic solvent in the presence of a base with heating to give compounds of the formula (I).

The compound of the formula (II) can be prepared as shown in the following reaction scheme:

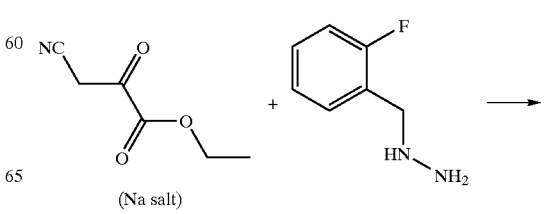

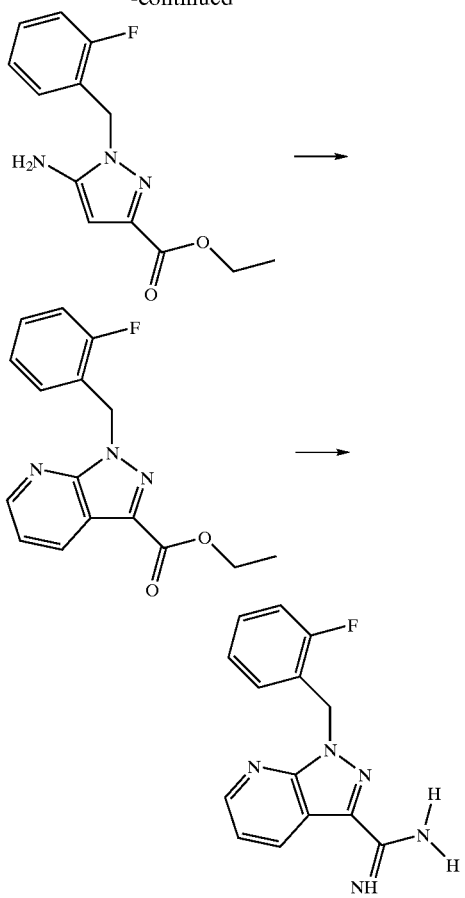

The compound of the formula (II) can be obtained in a multistage synthesis from the sodium salt of ethyl cyanopyruvate which is known from the literature (Borsche and Manteuffel, Liebigs. Ann. Chem. 1934, 512, 97). Reaction thereof with 2-fluorobenzylhydrazine with heating and under a protective gas atmosphere in an inert solvent such as dioxane results in ethyl 5-amino-1-(2-fluorobenzyl) pyrazole-3-carboxylate, which cyclizes to the corresponding pyridine derivative by reaction with dimethylaminoacrolein in acidic medium under a protective gas atmosphere and with heating. This pyridine derivative ethyl 1-(2-fluorobenzyl)-1H-pyrazolo[3,4-b]pyridine-3-carboxylate is converted by a multistage sequence consisting of conversion of the ester with ammonia into the corresponding amide, dehydration with a dehydrating agent such as trifluoroacetic anhydride to give the corresponding nitrile derivative, reaction of the nitrile derivative with sodium ethoxide and final reaction with ammonium chloride into the compound of the formula (II).

The compound of the formula (III) can be prepared from the compounds, which can be purchased (e.g. from Aldrich), t-butoxybis(dimethylamino)methane and methoxyacetonitrile by reacting these reactants preferably in equimolar amounts preferably under atmospheric pressure and stirring the reaction solution for several hours, for example 12 hours, at elevated temperature, for example 60–110° C., preferably 70–90° C., in particular 80° C.

The reaction of the compounds of the formulae (II) and (III) to give the compound of the formula (IV) can be carried out by employing the reactants in equimolar amounts or by using the compound of the formula (III) in slight excess in an organic solvent, for example an alcohol, preferably isoamyl alcohol, in the presence of a small amount of a base, for example an organic amine, in particular piperidine, preferably under atmospheric pressure and stirring the reaction solution for several hours, for example 12 hours, at elevated temperature, for example 60–130° C., preferably 80–120° C., in particular 110° C., and subsequent liberation of the hydroxyl group by reacting the compound obtained in this way with a preferably equimolar amount of a thiol such as, for example, thiophenol in the presence of a small amount of a base such as an alkali metal base, for example an alkali metal carbonate, preferably potassium carbonate, in an organic solvent such as, for example, 1-methyl-2-pyrrolidone, preferably under atmospheric pressure and stirring the reaction solution for several hours, for example 1 hour, at elevated temperature, for example 100–200° C., preferably 150–200° C.

The compound of the formula (IV) obtained in this way can be converted into the compounds of the formula (I) of the invention by reaction with an equimolar amount or of a slight excess of a sulfonyl compound of the formula $XSO_2R_2$. The reaction is carried out in the presence of a small amount of a base such as an organic amine, preferably pyridine, preferably under atmospheric pressure and stirring the reaction solution for several hours, for example 12 hours, at elevated temperature, for example 40–80° C., preferably 50–70° C. The sulfonyl compounds can be purchased or obtained in a manner known to the skilled worker.

The compounds of the invention of the general formula (I) show a valuable range of pharmacological effects which could not be predicted.

The compounds according to the invention of the general formula (I) bring about vasorelaxation and an inhibition of platelet aggregation and lead to a reduction in blood pressure and an increase in coronary blood flow. These effects are mediated by direct stimulation of soluble guanylate cyclase and an intracellular increase in cGMP. In addition, the compounds according to the invention of the general formula (I) enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transistorily and ischemic attacks, disturbances of peripheral blood flow, prevention of restenoses as after thrombolysis therapies, percutaneously transluminal angioplasties (PTAs), percutaneously transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, osteoporosis, gastroparesis and incontinence.

The compounds described in the present invention of the general formula (I) also represent active ingredients for controlling central nervous system diseases characterized by disturbances of the NO/cGMP system. They are suitable in particular for improving perception, concentration, learning or memory after cognitive impairments like those occurring in particular in association with situations/diseases/ syndromes such as mild cognitive impairment, age-associated learning and memory impairments, age-associated memory loss, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, vascular dementia, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The active ingredients are furthermore also suitable for controlling cerebral blood flow and thus represent effective agents for controlling migraine.

They are also suitable for the prophylaxis and control of the sequelae of cerebral infarctions such as stroke, cerebral ischemias and craniocerebral trauma. The compounds of the invention of the general formula (I) can likewise be employed for controlling states of pain.

In addition, the compounds of the invention have an anti-inflammatory effect and can therefore be employed as anti-inflammatory agents.

Furthermore, the invention encompasses the combination of the compounds of the invention of the general formula (I) with organic nitrates and NO donors.

Organic nitrates and NO donors for the purposes of the invention are generally substances which display their therapeutic effect via release of NO or NO species. Preference is given to sodium nitroprusside, nitroglycerine, isosorbide dinitrate, isosorbide mononitrate, molsidomine and SIN-1.

In addition, the invention encompasses the combination with compounds which inhibit breakdown of cyclic guanosine monophosphate (cGMP). These are in particular inhibitors of phosphodiesterases 1, 2 and 5; nomenclature of Beavo and Reifsnyder (1990), TiPS 11 pp. 150 to 155. These inhibitors potentiate the effect of the compound of the invention, and the desired pharmacological effect is increased.

BIOLOGICAL INVESTIGATIONS

Vasorelaxant Effect in vitro

Rabbits are stunned by a blow to the back of the neck and are exsanguinated. The aorta is removed, freed of adherent tissue, divided into rings 1.5 mm wide and put singly under tension in 5 ml organ baths containing carbogen-gassed Krebs-Henseleit solution at 37° C. with the following composition (mM): NaCl: 119; KCl: 4.8; $CaCl_2 \times 2\ H_2O$: 1; $MgSO_4 \times 7\ H_2O$; 1.4; $KH_2PO_4$: 1.2; $NaHCO_3$: 25; glucose: 10. The force of contraction is detected with Statham UC2 cells, amplified and digitized via A/D converters (DAS-1802 HC, Keithley Instruments Munich) and recorded in parallel on chart recorders. A contraction is generated by adding phenylephrine to the bath cumulatively in increasing concentration. After several control cycles, the substance to be investigated is investigated in each further run in increasing dosage in each case, and the height of the contraction is compared with the height of the contraction reached in the last preceding run. The concentration necessary to reduce the height of the control value by 50% ($IC_{50}$) is calculated from this. The standard application volume is 5 µl, and the DMSO content in the bath solution corresponds to 0.1%. The results are listed in table 1 below:

TABLE 1

Vasorelaxant effect in vitro

| Example No. | $IC_{50}$ [nM] |
|---|---|
| 1 | 700 |
| 2 | 580 |
| 3 | 300 |
| 4 | 710 |
| 5 | 520 |
| 7 | 440 |
| 10 | 2020 |

Determination of the Liver Clearance in vitro

Rats are anesthetized, heparinized, and the liver is perfused in situ via the portal vein. Primary rat hepatocytes are then obtained ex vivo from the liver using collagenase solution. $2 \cdot 10^6$ hepatocytes per ml were incubated at 37° C. with the same concentration in each case of the compound to be investigated. The decrease of the substrate to be investigated over time was determined bioanalytically (HPLC/UV, HPLC/fluorescence or LC/MSMS) at 5 points in time in each case in the period from 0–15 min after the start of incubation. From this, the clearance was calculated by means of the cell count and liver weight.

Determination of the Plasma Clearance in vivo

The substance to be investigated is administered as a solution intravenously to rats via the tail vein. At fixed points in time, blood is taken from the rats, heparinized and plasma is obtained therefrom by conventional measures. The substance is quantified bioanalytically in the plasma. The pharmacokinetic parameters are calculated from the plasma concentration-time courses determined in this way by means of conventional non-compartmental methods used for this purpose.

The present invention includes pharmaceutical preparations which, besides nontoxic, inert pharmaceutically suitable carriers, comprises the compounds of the invention of the general formula (I), and processes for producing these preparations.

The active ingredient may be present where appropriate in one or more of the carriers indicated above also in microencapsulated form.

The therapeutically effective compounds of the general formula (I) ought to be present in the pharmaceutical preparations mentioned above in a concentration of about 0.1 to 99.5, preferably of about 0.5 to 95, % by weight of the complete mixture.

The pharmaceutical preparations mentioned above may, apart from the compounds of the invention of the general formula (I), also comprise other active pharmaceutical ingredients.

It has generally proved advantageous both in human and in veterinary medicine to administer the active ingredient(s) of the invention in total amounts of about 0.01 to about 700, preferably 0.01 to 100, mg/kg of body weight per 24 hours, where appropriate in the form of a plurality of single doses, to achieve the desired results. A single dose comprises the active ingredient(s) of the invention preferably in amounts of about 0.1 to about 80, in particular 0.1 to 30, mg/kg of body weight.

The present invention is described in more detail below by means of nonrestrictive preferred examples. Unless indicated elsewhere, all quantitative data relate to percentages by weight.

EXAMPLES

Abbreviations

| | |
|---|---|
| RT: | room temperature |
| EA: | ethyl acetate |
| MCPBA: | m-chloroperoxybenzoic acid |
| BABA: | n-butyl acetate/n-butanol/glacial acetic acid/phosphate buffer pH 6 (50:9:25.25; org. phase) |
| DMF: | N,N-dimethylformamide |

Mobile Phases for the Thin-layer Chromatography

| | |
|---|---|
| T1 E1: | toluene-ethyl acetate (1:1) |
| T1 EtOH1: | toluene-methanol (1:1) |
| C1 E1: | cyclohexane-ethyl acetate (1:1) |
| C1 E2: | cyclohexane-ethyl acetate (1:2) |

Methods for Establishing the HPLC Retention Times

Method A (HPLC-MS):

| | |
|---|---|
| Eluent: | A = $CH_3CN$ B = 0.6 g 30% HCl/l $H_2O$ |
| Flow rate: | 0.6 ml/min |
| Column oven: | 50° C. |
| Column: | symmetry C18 2.1 * 150 mm |

Gradient:

| Time (min) | % A | % B | Flow rate (ml/min) |
|---|---|---|---|
| 0 | 10 | 90 | 0.6 |
| 4 | 90 | 10 | 0.6 |
| 9 | 90 | 10 | 0.8 |

Method B (HPLC):

| | |
|---|---|
| Eluent: | A = 5 ml $HClO_4$/l $H_2O$, B = $CH_3CN$ |
| Flow rate: | 0.75 ml/min |
| L-R temperature: | 30.00° C. 29.99° C. |
| Column: | Kromasil C18 60 * 2 mm |

Gradient:

| Time (min) | % A | % B |
|---|---|---|
| 0.50 | 98 | 2 |
| 4.50 | 10 | 90 |
| 6.50 | 10 | 90 |
| 6.70 | 98 | 2 |
| 7.50 | 98 | 2 |

Method C (HPLC):

| | |
|---|---|
| Eluent: | A = $H_3PO_4$ 0.01 mol/l, B = $CH_3CN$ |
| Flow rate: | 0.75 ml/min |
| L-R temperature: | 30.01° C. 29.98° C. |
| Column: | Kromasil C18 60 * 2 mm |

Gradient:

| Time (min) | % A | % B |
|---|---|---|
| 0.00 | 90 | 10 |
| 0.50 | 90 | 10 |
| 4.50 | 10 | 90 |
| 8.00 | 10 | 90 |
| 8.50 | 90 | 10 |
| 10.00 | 90 | 10 |

Method D (chiral HPLC):

| | |
|---|---|
| Eluent: | 50% isohexane, 50% ethanol |
| Flow rate: | 1.00 ml/min |
| Temperature: | 40° C. |
| Column: | 250 * 4.6 mm, packed with Chiralcel OD, 10 μm |

Method E (HPLC-MS):

| | |
|---|---|
| Eluent: | A = $CH_3CN$ B = 0.3 g 30% HCl/l $H_2O$ |
| Flow rate: | 0.9 ml/min |
| Column oven: | 50° C. |
| Column: | Symmetry C18 2.1*150 mm |

Gradient:

| Time (min) | % A | % B | Flow rate (ml/min) |
|---|---|---|---|
| 0 | 10 | 90 | 0.9 |
| 3 | 90 | 10 | 1.2 |
| 6 | 90 | 10 | 1.2 |

STARTING COMPOUNDS

I. Synthesis of 3,3-bis(dimethylamino)-2-methoxypropionitrile

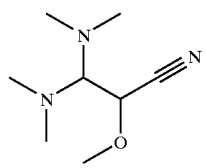

40.0 g (229.5 mmol) of ter-butoxybis(dimethylamino)methane and 16.3 g (229.5 mmol) of methoxyacetonitrile are stirred at 80° C. overnight. For working up, volatile material is stripped off in a rotary evaporator, and the residue is distilled under high vacuum in a Kugelrohr at 140° C. The product contains, according to the NMR spectrum (300 MHz, $D_6$-DMSO) the enamine as E/Z mixture produced by elimination of dimethylamine. The product mixture is employed without further purification in the next reaction.

Yield: 24.7 g (60%).

II. Synthesis of 1-(2-fluorobenzyl)-1H-pyrazolo[3,4-b]pyridine-3-carboxamidine

2A) Ethyl 5-amino-1-(2-fluorobenzyl)pyrazole-3-carboxylate

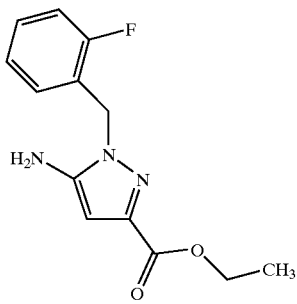

111.75 g (75 ml, 0.98 mol) of trifluoroacetic acid are added to 100 g (0.613 mol) of the sodium salt of ethyl cyanopyruvate (prepared in analogy to Borsche and Manteuffel, Liebigs Ann. 1934, 512, 97) while stirring efficiently in 2.5 l of dioxane at room temperature under argon, and the mixture is stirred for 10 min, during which most of the precursor dissolves. Then 85.93 g (0.613 mol) of 2-fluorobenzylhydrazine are added, and the mixture is boiled overnight. After cooling, the sodium trifluoroacetate crystals which have separated out are filtered off with suction and washed with dioxane, and the crude solution is reacted further.

2B) Ethyl 1-(2-fluorobenzyl)-1H-pyrazolo[3,4-b]pyridine-3-carboxylate

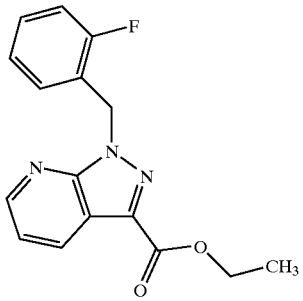

The solution obtained from 2 A) is mixed with 61.25 ml (60.77 g, 0.613 mol) of dimethylaminoacrolein and 56.28 ml (83.88 g, 0.736 mol) of trifluoroacetic acid and boiled under argon for 3 days. The solvent is then evaporated in vacuo, and the residue is poured into 2 l of water and extracted three times with 1 l of ethyl acetate each time. The combined organic phases are dried with magnesium sulfate and concentrated in a rotary evaporator. Chromatography is carried out on 2.5 kg of silica gel, eluting with a toluene/toluene-ethyl acetate=4:1 gradient. Yield: 91.6 g (49.9% of theory over two stages).

Melting point 85° C.

$R_f$ (SiO$_2$, T1E1): 0.83.

2C) 1-(2-Fluorobenzyl)-1H-pyrazolo[3,4-b]pyridine-3-carboxamide

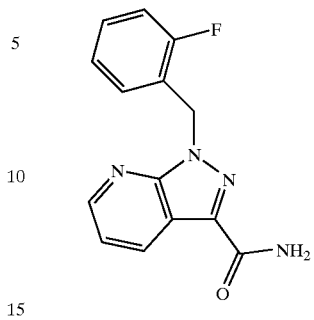

10.18 g (34 mmol) of the ester obtained in example 2 B) are introduced into 150 ml of methanol saturated with ammonia at 0–10° C. Stirring at room temperature for two days is followed by concentration in vacuo.

$R_f$ (SiO$_2$,T1E1): 0.33.

2D) 3-Cyano-1-(2-fluorobenzyl)-1H-pyrazolo[3,4-b]pyridine

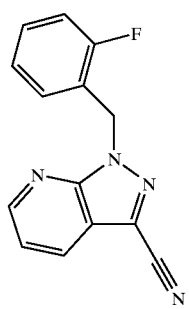

36.1 g (133 mmol) of 1-(2-fluorobenzyl)-1H-pyrazolo[3,4-b]pyridine-3-carboxamide from example 2 C) are dissolved in 330 ml of THF, and 27 g (341 mmol) of pyridine are added. Then, over the course of 10 min, 47.76 ml (71.66 g, 341 mmol) of trifluoroacetic anhydride are added, during which the temperature rises to 40° C. The mixture is stirred at room temperature overnight. The mixture is then poured into 1l of water and extracted three times with 0.5l of ethyl acetate each time. The organic phase is washed with saturated sodium bicarbonate solution and with 1 N HCl, dried with MgSO4 and concentrated in a rotary evaporator.

Yield: 33.7 g (100% of theory).

Melting point: 81° C.

$R_f$ (SiO$_2$, T1E1): 0.74.

2E) Methyl (2-fluorobenzyl)-1H-pyrazolo[3,4-b]pyridine-3-carboximidate

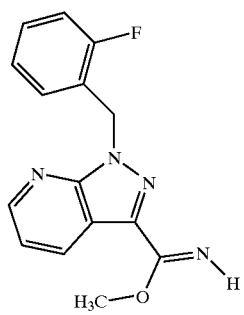

30.37 g (562 mmol) of sodium methoxide are dissolved in 1.5 l of methanol, and 36.45 g (144.5 mmol) of 3-cyano-1-(2-fluorobenzyl)-1H-pyrazolo[3,4-b]pyridine (from example 2 D) are added. The solution obtained after stirring at room temperature for 2 hours is employed directly for the next stage.

2F) 1-(2-Fluorobenzyl)-1H-pyrazolo[3,4-b]pyridine-3-carboxamidine

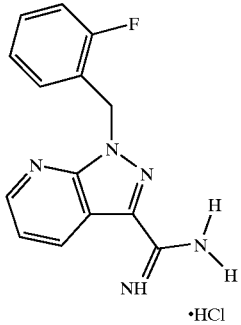

The solution of methyl (2-fluorobenzyl)-1H-pyrazolo[3,4-b]pyridine-3-carboximidate in methanol obtained from example 2 E) is mixed with 33.76 g (32.19 ml, 562 mmol) of glacial acetic acid and 9.28 g (173 mmol) of ammonium chloride and stirred under reflux overnight. The solvent is evaporated in vacuo, the residue is thoroughly triturated with acetone, and the precipitated solid is filtered off with suction.

$^1$H-NMR (d$_6$-DMSO, 200 MHz): δ=5.93 (s, 2H); 7.1–7.5 (m, 4H); 7.55 (dd, 1H); 8.12 (dd, 1H); 8.30 (dd, 1H); 9.5 (bs, 4H exchangeable) ppm.

MS (EI): m/z=270.2 (M-HCl).

III. Synthesis of 2-[1-(2-fluorobenzyl)-1H-pyrazolo[3,4-b]pyridin-3-yl]-5-methoxy-4-pyrimidinylamine

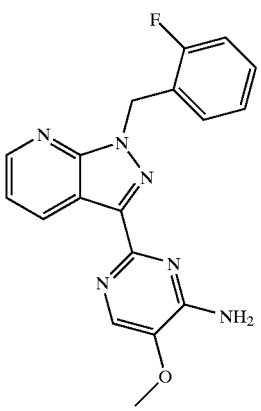

46.8 g (134.8 mmol) of 1-(2-fluorobenzyl)-1H-pyrazolo[3,4-b]pyridine-3-carboximidamide from example II are dissolved in isoamyl alcohol. To this are added 24.7 g (144.2 mmol) of 3,3-bis(dimethylamino)-2-methoxypropionitrile from example I and 1.15 g (1.33 ml, 13.5 mmol) of piperidine, and the mixture is left to stir at 110° C. for 3 days. For working up, it is cooled to 0° C., and the precipitated product is filtered off with suction, washed thoroughly with cold diethyl ether and dried in a vacuum oven at 50° C.

Yield: 25.4 g (52.7%).

R$_f$: 0.34 (dichloromethane/methanol 20:1).

$^1$H-NMR: (400 MHz, d$_6$-DMSO), δ=3.89 (2, 3H, OCH$_3$), 5.79 (s, 2H, CH$_2$), 6.93 (br. s, 2H, NH$_2$), 7.10–7.26 (m, 3H, Ar—H), 7.31–7.39 (m, 2H, Ar—H), 7.98 (s, 1H, pyrimidine-H), 8.61 (dd, 1H, pyridine-H), 8.92 (dd, 1H, pyridine-H).

MS: (ESI pos.), m/z=350.9 ([M+H]$^+$), 700.8 ([2M+H]$^+$).

IV. Synthesis of 4-amino-2-[1-(2-fluorobenzyl)-1H-pyrazolo[3,4-b]pyridin-3-yl]-5-pyrimidinol

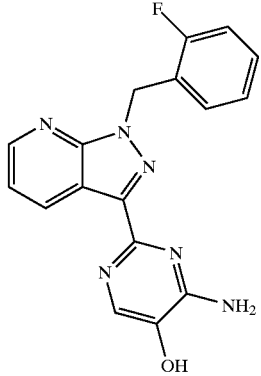

25.3 g (72.2 mmol) of 2-[1-(2-fluorobenzyl)-1H-pyrazolo[3,4-b]pyridin-3-yl]-5-methoxy-4-pyrimidinylamine from example III are dissolved in 500 ml of 1-methyl-2-pyrrolidone. To this are added 7.96 g (7.42 ml, 72.2 mmol) of thiophenol and 2.50 g (18.1 mmol) of potassium carbonate, and the mixture is left to stir at 190° C. for about 1 h. For working up, the solvent is condensed off, and the residue is mixed with half-conc. ammonium chloride solution and extracted three times with ethyl acetate. Most of the product precipitates during this. It is filtered off with suction and dried in a vacuum oven at 50° C.

Yield: 18.1 g (72.3%).

R$_f$: 0.44 (dichloromethane/methanol 10:1).

$^1$H-NMR: (300 MHz, D$_6$-DMSO), δ=5.78 (s, 2H, CH$_2$), 6.66 (br. s, 2H, NH$_2$), 7.09–7.38 (m, 5H, Ar—H), 7.82 (s, 1H, pyrimidine H), 8.60 (dd, 1H, pyridine H), 8.92 (dd, 1H, pyridine H), 9.4–10.2 (br. s, 1H, OH).

MS: (ESI pos.), m/z=337.3 ([M+H]$^+$), 673.3 ([2M+H]$^+$).

EXAMPLES 1. 4-Amino-2-[1-(2-fluorobenzyl)-1H-pyrazolo[3,4-b]pyridin-3-yl]-5-pyrimidinyl chloromethanesulfonate

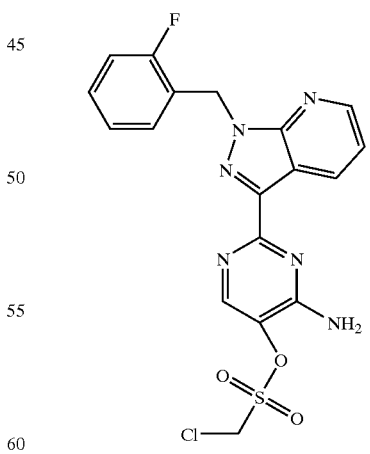

400 mg (1.19 mmol) of 4-amino-2-[1-(2-fluorobenzyl)-1H-pyrazolo[3,4-b]pyridin-3-yl]5-pyrimidinol from example IV were suspended in 8.0 ml of pyridine, and 186.1 mg (1.25 mmol) of chloromethanesulfonyl chloride were added. The suspension was stirred at 60° C. overnight and then water was added to the mixture. The resulting precipitate was filtered off with suction, washed several times with water and dried under high vacuum.

Yield: 480 mg (77.3%).

¹H-NMR: (400 MHz, D₆-DMSO, δ=5.76 (s, 2H, CH₂), 5.82 (s, 2H, CH₂), 6.66 (br. s, 2H, NH₂), 7.10–7.26 (m, 3H, Ar—H), 7.30–7.42 (m, 2H, Ar—H), 7.59 (br. s, 2H, NH₂), 8.31 (s, 1H, pyrimidine H), 8.65 (dd, 1H, pyridine H), 8.93 (dd, 1H, pyridine H).

MS: (ESI pos.), m/z=449 ([M+H]⁺), 897 ([2M+H]⁺).

The following were prepared in an analogous manner:

| Example | Formula | Yield (%) | 1H-NMR |
|---|---|---|---|
| 2 (from IV and methyl-sulfonyl chloride) | | 89 | (300 MHz, CDCl₃): δ= 3.51(s, 3H), 5.83(s, 2H), 7.06–7.28(m, 3H), 7.31–7.45(m, 2H), 7.58(bs, 2H), 8.28(s, 1H), 8.65(dd, J= 4.5 Hz, J=1.5 Hz, 1H), 8.94(dd, j=8.1 Hz, J=1.5 Hz, 1H). |
| 3 (from IV and ethyl-sulfonyl chloride) | | 89 | (300 MHz, DMSO-d₆, δ = 1.37(t, J=7.4 Hz, 3H), 3.71(q, J=7.4 Hz, 2H), 5.83(s, 2H), 7.03–7.28 (m, 3H), 7.29–7.44(m, 2H), 7.52(bs, 2H), 8.29(s, 1H), 8.65(dd, J=4.5 Hz, J= 1.3 Hz, 1H), 8.93(dd, J= 8.1 Hz, J=1.3 Hz, 1H). |
| 4 (from IV and cyclo-propyl-sulfonyl chloride) | | 90 | (300 MHz, DMSO-d₆): d= 1.03–1.12(m, 2H), 1.14–1.24(m, 2H), 3.21–3.39 (m, 1H), 5.83(s, 2H), 7.05–7.28(m, 2H), 7.30–7.44 (m, 2H), 7.57(bs, 2H), 8.29 (s, 1H), 8.65(dd, J=4.5 Hz, J=1.3 Hz, 1H), 8–64 (dd, J=7.9 Hz, J=1.3 Hz, 1H). |

-continued

| Example | Formula | Yield (%) | 1H-NMR |
|---|---|---|---|
| 5 (from IV and isopropyl-sulfonyl chloride) | | 83 | (300 MHz, DMSO-d₆): d= 1.45(d, J=6.8 Hz, 6H), 4.04(sept, J=6.8 Hz, 1H), 5.83(s, 2H), 7.01–7.28 (m, 3H), 7.29–7.59(m, 4H), 8.29(s, 1H), 8.65(dd, J=4.4 Hz, J=1.5 Hz, 1H), 8.94(dd, J=8.1 Hz, J=1.5 Hz, 1H). |
| 6 (from IV and n-pentyl-sulfonyl chloride) | | 32 | (300 MHz, DMSO-d₆): d= 0.87(t, J=7.0 Hz, 3H), 1.23–1.47=(m, 4h), 1.81 (quint, J=7.6 Hz, 2H), 3.70(t, J=7.7 Hz, 2H), 5.83(s, 2H), 7.05–7.27 (m, 3H), 7.31–7.46(m, 2H), 7.53(bs, 2H), 8.28(s, 2H), 8.65(dd, J=4.4 Hz, J= 1.5 Hz, 1H), 8.93(dd, J= 8.1 Hz, J=1.5 Hz, 1H). |
| 7 (from IV and 1,1,1-trifluoro-4-butyl-sulfonyl chloride) | | 69 | (300 MHz, DMSO-d₆): d= 2.05(quint, J=7.9 Hz, 2H), 2.35–2.59(m, 2H), 3.83(t, J=7.7 Hz, 2H), 5.83(s, 2H), 7.06–7.28 (m, 3H), 7.29–7.44(m, 2H), 7.59(bs, 2H), 8.30(s, 2H), 8.65(dd, J=4.5 Hz, J= 1.5 Hz, 1H), 8.93(dd, J= 8.1 Hz, J=1.5 Hz, 1H). |

-continued

| Example | Formula | Yield (%) | 1H-NMR |
| --- | --- | --- | --- |
| 8 (from IV and n-butyl-sulfonyl chloride) | | 99 | (300 MHz, DMSO-d₆): d= 0.91(t, J=7.4Hz, 3H), 1.44(sex, J=7.4 Hz, 2H), 1.79(quint, J=7.4 Hz, 2H), 3.71(t, J=7.5 Hz, 2H), 5.83(s, 2H), 7.08–7.27(m, 3H), 7.31–7.43 (m, 2H), 7.53(bs, 2H), 8.28 (s, 1H), 8.65(dd, J=4.5 Hz, J=1.7 Hz, 1H), 8.93 (dd, J=8.1 Hz, J=1.7 Hz, 1H). |
| 9 (from IV and n-propyl-sulfonyl chloride) | | 98 | (300 MHz, DMSO-d₆): d= 1.02(t, J=7.4 Hz, 3H), 1.84(sex, J=7.4 Hz, 2H), 3.68(t, J=7.6 Hz, 2H), 5.83(s, 2H), 7.08–7.27 (m, 3H), 7.31–7.43(m, 2H), 7.53(bs, 2H), 8.28(s, 1H), 8.65(dd, J=4.5 Hz, J=1.7 Hz, 1H), 8.93(dd, J= 8.1 Hz, J=1.7 Hz, 1H). |
| 10 (from IV and phenyl-sulfonyl chloride) | | 35.4 | (300 MHz, DMSO-d₆): δ = 5.80(s, 2H), 7.08–7.24 (m, 7H), 7.66(t, J=7.6 Hz, 2H), 7.78–7.87(t, J=7.5 Hz, 1H), 7.97–8.03(m, 2H), 8.06(s, 1H), 8.64(dd, J=4.3 Hz, J=1.5 Hz, 1H), 8.88(dd, J=8.1 Hz, J=1.7 Hz, 1H). |

We claim:

1. A compound of the formula (I)

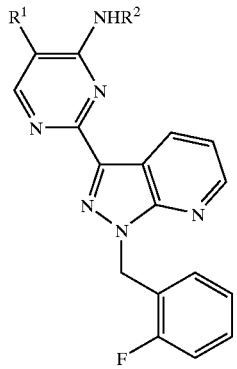

(I)

in which

R¹ is a radical of the formula —O—SO₂—R³,
where
R³ is a radical from the group consisting of optionally substituted $C_{1-6}$-alkyl, optionally substituted $C_{3-8}$-cycloalkyl, or optionally substituted phenyl;

R² is H, optionally substituted $C_{1-6}$-alkyl-CO or optionally substituted $C_{1-6}$-alkyl-SO₂—;

or a salt, stereoisomer, tautomer or hydrate thereof.

2. The compound as claimed in claim 1,
in which
R¹ is a radical of the formula —O—SO₂—R³,
where
R³ is a radical selected from the group consisting of $C_{1-6}$-alkyl which is optionally substituted by one to three halogen radicals, and $C_{3-8}$-cycloalkyl; and
R² is H, $C_{1-6}$-alkyl-CO which is optionally substituted by one to three halogen radicals, or $C_{1-6}$-alkyl-SO₂— which is optionally substituted by one to three halogen radicals.

3. The compound as claimed in claim 1,
in which
R¹ is a radical of the formula —O—SO₂—R³,
where
R³ is a radical selected from the group consisting of methyl, ethyl, n-propyl, isopropyl, n-butyl, n-pentyl, 1,1,1-trifluoro-4-n-butyl, chloromethyl and cyclopropyl; and
R² is H or CH₃CO.

4. A process for preparing compounds of the formula I, comprising reacting a compound of the formula (II)

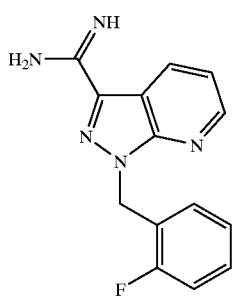

(II)

with a compound of the formula (III)

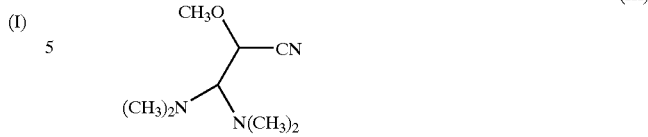

(III)

in an organic solvent in the presence of a base with heating and subsequent conversion of the ether group in the free hydroxyl group to give a compound of the formula (IV)

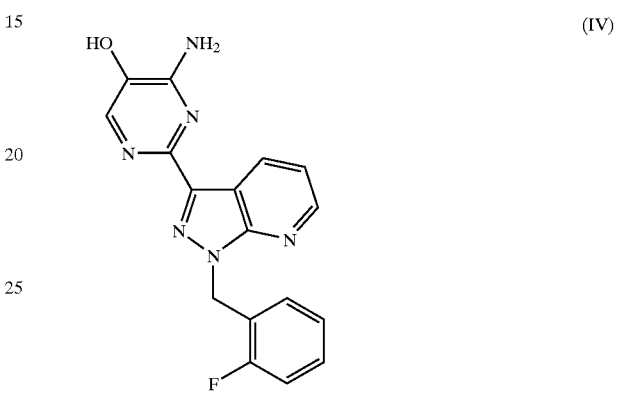

(IV)

and subsequent reaction with a compound of the formula X—SO₂—R² in which
X is a leaving group which can be replaced by a hydroxyl group; and
R² has the meaning indicated in claim 1;
in an organic solvent in the presence of a base with heating to give a compound of the formula (I).

5. A pharmaceutical composition comprising at least one compound of the formula (I) as claimed in claim 1 plus a pharmaceutically acceptable carrier.

6. A pharmaceutical composition comprising at least one compound of the formula (I) as claimed in claim 1 in combination with at least one organic nitrate or NO donor.

7. A pharmaceutical composition comprising at least one compound of the formula (I) as claimed in claim 1 in combination with at least one compound which inhibits the breakdown of cyclic guanosine monophosphate (cGMP).

8. A method for the treatment of hypertension comprising administering an effective amount of a compound of general formula (I) as claimed in claim 1.

9. A method for the treatment of sexual dysfunction comprising administering an effective amount of a compound of general formula (I) as claimed in claim 1.

10. The method as claimed in claim 8 or claim 9, where the compound of the general formula (I) as claimed in claim 1 is employed in combination with at least one organic nitrate or NO donor or in combination with at least one compound which inhibits the breakdown of cyclic guanosine monophosphate (cGMP).

* * * * *